United States Patent [19]

Hermann et al.

[11] 4,371,548

[45] Feb. 1, 1983

[54] DETERGENT-OIL BATH ADDITIVES

[75] Inventors: Claus Hermann, Baden-Baden; Helmut Krings, Achern-Oensbach, both of Fed. Rep. of Germany

[73] Assignee: Lingner and Fischer GmbH, Fed. Rep. of Germany

[21] Appl. No.: 188,066

[22] Filed: Sep. 17, 1980

[30] Foreign Application Priority Data

Sep. 22, 1979 [DE] Fed. Rep. of Germany ....... 7932944

[51] Int. Cl.$^3$ .............................................. A61K 7/00
[52] U.S. Cl. ............................ 424/365; 252/DIG. 5; 252/DIG. 13; 424/70; 424/358; 424/359
[58] Field of Search ................ 424/70, 358, 359, 365; 252/DIG. 5, DIG. 13, 551, 121

[56] References Cited

U.S. PATENT DOCUMENTS

| | | | |
|---|---|---|---|
| 3,533,955 | 10/1970 | Pader | 252/DIG. 5 |
| 3,562,170 | 2/1971 | Zorayan | 252/DIG. 5 |
| 4,115,548 | 9/1978 | Marsh | 424/359 |
| 4,130,497 | 12/1978 | Oneto | 252/89 R |
| 4,172,887 | 10/1979 | Vanlerberghe | 424/70 |

FOREIGN PATENT DOCUMENTS

| | | |
|---|---|---|
| 2750731 | 5/1979 | Fed. Rep. of Germany ........ 424/70 |
| 2758202 | 7/1979 | Fed. Rep. of Germany . |
| 797119 | 6/1958 | United Kingdom . |
| 2010832 | 7/1979 | United Kingdom .................. 424/70 |

OTHER PUBLICATIONS

Chambers, Soap, Perf & Cos., vol. 49, No. 3, Mar. 1976, p. 89.
Janistyn, Kosmetischen, Grundstoffe, Handbook der Kosmetika & Riechstoffe, 3, DE, Heidelberg, Hulhig, Verlag, 1978, Bandl, pp. 597–598.
Balsam & Sagarin, Cos. Sci. & Tech., Wiley-Intersci., NY, 1972, 2nd ed., vol. 12, p. 680.
Hawley, The Condensed Chem. Dict., Van Nostrand Reinhold Co., NY, 8th ed., 1971, p. 594.

*Primary Examiner*—Anna P. Fagelson
*Attorney, Agent, or Firm*—Jacobs & Jacobs

[57] ABSTRACT

A bath additive or shower gel, comprising 20 to 70% by weight of a detergent blend (consisting of 10 to 90% by weight of an amine $C_{8-18}$ fatty alcohol sulphate (optionally ethoxylated) and a metal or ammonium ethoxylated $C_{8-18}$ fatty alcohol sulphate) and 20 to 60% by weight of a cosmetically acceptable oil, gives improved oil deposition.

9 Claims, No Drawings

DETERGENT-OIL BATH ADDITIVES

This invention relates to skin-care bath additive compositions, for example bath liquid or shower gel compositions, and to a process for their preparation.

Optimal detergent-oil bath additives for consumer satisfaction would ideally be homogeneous (for attractive appearance, for not requiring shaking before use and for reproducible results), have a good washing performance with high foaming, and deposit a maximised proportion of the oil present on the skin.

Hitherto the interaction of the detergent and oil in such products has lead to these criteria being mutually exclusive. Thus homogeneous additives generally have to sacrifice adequate oil deposition for good foaming or vice versa. Additives combining adequate foaming and deposition are usually two-phase and suffer from the above disadvantages of non-homogeneity.

U.S. Pat. No. 4,130,497 discloses homogeneous bath additives having adequate foaming and oil deposition properties, but this is achieved using a detergent blend containing a relatively expensive special detergent and the compositions suffer from a relatively restricted permissible oil and/or water content above which phase instability occurs.

Surprisingly we have now found that a homogenous oil-detergent bath additive can be prepared using relatively cheap, more conventional detergents, which compositions have good foaming properties, have a higher permissible oil and/or water content and give substantially better oil deposition on the skin than the homogeneous additives of the prior art.

Accordingly, this invention provides a skin-care bath additive composition, which composition comprises (i) 20 to 70% by weight of the composition of a detergent blend consisting of:

(a) 10 to 90% by weight of the blend of at least one amine $C_{8-18}$ fatty alcohol sulphate optionally ethoxylated in the $C_{8-18}$ fatty alcohol sulphate anion, and (b) 90 to 10% by weight of the blend of a metal ethoxylated $C_{8-18}$ fatty alcohol sulphate or ammonium ethoxylated $C_{8-18}$ fatty alcohol sulphate, and (ii) 20 to 60% by weight of the composition of a cosmetically acceptable oil.

Whilst the detergent blend may form 20 to 70% by weight of the total composition, it is more usually 40 to 65%.

Within the detergent blend the amine $C_{8-18}$ fatty alcohol sulphate (optionally ethoxylated), or the mixture of such salts, forms 10 to 90% by weight of the detergent blend preferably 60 to 80%.

The metal or ammonium ethoxylated $C_{8-18}$ fatty alcohol ether sulphate forms the balance of the detergent blend, that is 90 to 10% by weight of the detergent blend, preferably 40 to 20%.

Whilst the cosmetically acceptable oil forms 20 to 60% by weight of the total composition, it is more usually 25 to 45%.

Within the detergent blend the $C_{8-18}$ fatty alcohol sulphate anions (ethoxylated as appropriate) are preferably $C_{12-15}$ fatty alcohol sulphate anions, ethoxylated as appropriate.

Where these anions are ethoxylated they usually contain an average of 1 to 5 moles ethylene oxide per mole of fatty alcohol sulphate, preferably an average of 2 to 3 moles ethylene oxide per mole.

It will be appreciated that, as is conventional in the detergent art, although each component of the detergent blend is described as a single salt, it is in fact usually a mixture of such salts having a common cation, the anions of the salts differing in carbon content. As in also usual in the art however these anions will normally be derived from the same fatty alcohol 'cut', for example the $C_{12-13}$ cut or the $C_{12-14}$ cut, the number of different anions varying with the breadth of cut. This will also be true when the anions are ethoxylated.

It will also be appreciated that, as is usual, when these anions are ethoxylated, the degree of ethoxylation will vary throughout a given blend component, and the stated degree of ethoxylation represents an average degree.

Amine salts which may be used in the present detergent blends include the salts of mono- and polyalkylamines such as diethylamine, mono- and polyalkanolamines such as ethanolamine, diethanolamine, isopropanolamine, and diisopropanolamine, and mixed alkanolalkylamines such as butylethanolamine and dibutylethanolamine or ethylethanolamine or diethylethanolamine.

Preferred amines include diethylamine and monobutylethanolamine.

Preferably the detergent blend contains a mixture of salts of more than one amine.

Suitable metal salts in the present detergent blends include alkali metal salts, preferably the sodium and potassium salts, and magnesium and calcium salts, preferably the magnesium salts. Sodium salts are particularly preferred.

Cosmetically acceptable oils which may be used in the present invention include natural oils such as vegetable oils, for example castor oil, olive oil, safflower oil, rapeseed oil or sunflower oil; naturally occurring $C_{8-12}$ fatty alcohols and $C_{12-20}$ alcohols liquid at room temperature (generally branched-chain and/or unsaturated alcohols) such as oleyl alcohol, isostearyl akohol and 2-octyldodecanol (Eutanol G); and synthetic oils such as esters of long-chain fatty acids or alcohols, for example isopropyl myristate, isopropyl palmitate, lauryl caprate, or $C_{8-12}$ fatty acid triglycerides liquid at room temperature.

Preferred oils include castor oil and synthetic liquid $C_{8-12}$ fatty acid triglycerides.

It will be appreciated that, whilst it is not essential, the compositions of the present invention may also contain water. We have found that water should only be present as not in excess of 15% by weight of the total composition, to prevent phase separation.

The compositions may also contain additives which are conventional in the toiletries art, such as perfumes, colorants, preservatives and solubilisers. Suitable solubilisers include ethoxylated fatty acids and fatty alcohols and coconut acid diethanolamides.

The viscosity of the compositions may be adjusted as is conventional by incorporating additives such as ethanol, isopropanol, ethanol, isopropanol, ethylene or propylene glycol, glymes, ethoxylated fatty alcohols and fatty acids and coconut fatty acid ethanolamides.

In this way the compositions may be presented as liquids for baths or as shower gels.

The bath liquid compositions of the present invention will typically be used at the rate of 20 ml. composition per 200 liters of bath water. The shower gels will typically be used in a single 5 ml. application.

One such process comprises mixing the detergents with the oils or oils under stirring.

The present invention also provides a process for the preparation of the present compositions, which process comprises bringing into association the stated ingredients in the stated proportions.

One such process comprises mixing the detergent with the oil under stirring.

The following Examples illustrate the preparation of compositions according to the present invention.

'%' therein means '% by weight of the composition'.

The following Experiment illustrates the oil deposition and foaming properties of the compositions according to the present invention.

EXAMPLE 1

A composition of the following components was prepared by the methods set out below:

|  | % |
|---|---|
| Sodium $C_{12-13}$ alkyl ether sulphate (70% actives) (average 2-3 moles ethylene oxide per mole) | 23.6 |
| Mixture of diethylammonium and butylethanolammonium $C_{12-14}$ alkyl ether sulphate (average 2-3 moles ethylene oxide per mole) | 37.15 |
| Castor oil | 30.00 |
| Polyethylene glycol (PEG 400) | 4.00 |
| Isopropanol | 1.00 |
| Perfume, preservative, colorant, etc. | 4.25 |

The following operations were carried out at room temperature. The perfume, preservative colorants etc. were added to the castor oil with stirring, and stirring was continued to dissolution. The detergents were then added to the oil mixture and dissolved under stirring. These were followed by the glycol and isopropanol, and the resultant composition was stirred to homogeneity.

EXAMPLE 2

A composition differing from that of Example 1 in containing synthetic $C_{8-12}$ fatty acid triglyceride in place of castor oil was prepared by the methods of Example 1.

EXPERIMENT

The compositions of the Examples were evaluated for the quantity of oil left on the skin after bathing and for their foaming.

1. Oil deposition, test procedure

The forearms of each of ten human volunteers were each dipped in one of two separate vessels, each vessel containing 1.5 g of the bath additive composition dispersed in 7.5 l. of water at 40° C. (equivalent to 20 g. composition in 100 l. water). The forearms were then dried with a blow drier and a defined area on each forearm was extracted twice by contacting with acetone for 1 minute. An identical control extraction was carried out on untreated forearms to determine extracted natural skin lipid. Finally, the quantity of adsorbed oil relative to extracted natural skin lipid was determined by quantitative thin layer chromatography. The results are shown in the following Table.

2. Foaming, test procedure

This property was assessed by evaluating foaming by two methods, firstly that of Ross and Miles (Oil and Soap, 1941, May, 99-102), and secondly the so-called bath-tub procedure which more resembles the conditions of actual use.

The bath-tub procedure consists of adding water at constant pressure via a water inlet to a bath tub of defined volume containing a known volume of bath-additive composition. The foam formed at the area of contact of inlet stream and liquid in the bath is spread evenly over the liquid surface. The bath tub is provided with a small 'harrow' the points of the tines of which touch the liquid surface and the tines of which are graduated in cm foam height. This is used to measure the mean foam height on the surface of the bath-tub liquid at 5 and 20 minutes after the final bath volume has been reached.

In the present test 12 g. composition per 200 l. water at 40° C. were used. Water was admitted at 3.5 bar via a 12 mm i.d. inlet.

3. Results

The results of the above tests were as follows:

TABLE

| Composition according to Example | 1 | 2 |
|---|---|---|
| mean quantity of castor oil ($\mu$g/100 cm$^2$ of skin) left on skin | 506 |  |
| mean quantity of $C_8$-$C_{12}$—fatty acid triglyceride ($\mu$g/100 cm$^2$ of skin) left on skin |  | 2579 |
| foam Ross and Miles (ml after 1 minute) | 110 | 95 |
| foam height, bath-tub procedure (cm) |  |  |
| after 5 minutes | 4,8 | 4,6 |
| after 20 minutes | 3,8 | 4,0 |

We claim:

1. A homogeneous, detergent-oil skin-care bathing composition having foaming and oil-deposition properties, which comprises;
   (i) from 20 to 70% by weight of the composition of a detergent blend consisting of:
      (a) from 10 to 90% by weight of the blend of at least one amine $C_{8-18}$ fatty alcohol sulphate optionally ethoxylated in the $C_{8-18}$ fatty alcohol sulphate anion, and
      (b) from 90 to 10% by weight of the blend of a metal ethoxylated $C_{8-18}$ fatty alcohol sulphate or ammonium ethoxylated $C_{8-18}$ fatty alcohol sulphate; and
   (ii) from 20 to 60% by weight of the composition of a cosmetically acceptable oil.

2. The composition according to claim 1 wherein the detergent blend forms 40 to 60% by weight of the composition and comprises from 60 to 80% by weight of the blend of the amine $C_{1-18}$ fatty alcohol sulphate and 40 to 20% by weight of the blend of the metal or ammonium ethoxylated $C_{8-18}$ fatty alcohol sulphate and the cosmetically acceptable oil forms 25 to 45% by weight of the composition.

3. The composition according to claim 1 wherein the optionally ethoxylated amine fatty alcohol sulphate is $C_{12-15}$ alcohol sulphate.

4. The composition according to claim 1 wherein the amine fatty alcohol sulphate is ethoxylated with 2 or 3 moles of ethylene oxide per mole.

5. The composition according to claim 1 wherein the amine is diethylamine or monobutylethanolamine.

6. The composition according to claim 1 wherein the metal ethoxylated fatty alcohol sulphate is a sodium, potassium, magnesium or calcium.

7. The composition according to claim 1 wherein the cosmetically acceptable oil is caster oil or synthetic liquid $C_{8-12}$ fatty acid triglyeride.

8. The composition according to claim 1 in the form of a bath additive or shower gel.

9. The composition according to claim 1 which further comprises water to a maximum of 15% by weight of the composition and perfume, colorant, preservative and/or solubilizer.

* * * * *